United States Patent

Scheker

[11] Patent Number: 5,951,604
[45] Date of Patent: Sep. 14, 1999

[54] DISTAL RADIOULNAR JOINT PROSTHESIS

[75] Inventor: Luis R. Scheker, Glenview, Ky.

[73] Assignee: Avanta Orthopedics, Inc., San Diego, Calif.

[21] Appl. No.: 09/001,767

[22] Filed: Dec. 31, 1997

[51] Int. Cl.[6] .................................................. A61F 2/42
[52] U.S. Cl. ............................................................. 623/21
[58] Field of Search ........................................ 623/21, 18

[56] References Cited

U.S. PATENT DOCUMENTS

| | | | |
|---|---|---|---|
| 4,180,871 | 1/1980 | Hamas | 623/21 |
| 4,229,841 | 10/1980 | Youm et al. | |
| 4,349,922 | 9/1982 | Agee . | |
| 5,108,444 | 4/1992 | Branemark | 623/21 |
| 5,133,762 | 7/1992 | Branemark | 623/21 |
| 5,782,926 | 7/1998 | Lamprecht | 623/21 |

FOREIGN PATENT DOCUMENTS

| | | | |
|---|---|---|---|
| 2660856 | 10/1991 | France | 623/21 |
| 2269752 | 1/1994 | United Kingdom | 623/21 |

OTHER PUBLICATIONS

*Sutter Implants for the Hand and Forearm,* brochure by Sutter Corporation; 4 pages; dated Feb. 12, 1990.
Brand, Paul W. M.B., B.S., F.R.C.S. and Hollister, Anne M.D., *Clinical Mechanics of the Hand,* Second Edition, 1993 by Mosby—Year Book, Inc., St. Louis, MO.

*Primary Examiner*—Michael J. Milano
*Attorney, Agent, or Firm*—Nydegger & Associates

[57] ABSTRACT

A prosthesis for the distal radioulnar joint of a patient includes an elongated rod which is formed with a pin at one end, and which has a body portion that can be attached to the ulna of the patient. Also included is a ball which is formed with a channel for receiving the pin of the rod therein to establish a relative translational motion between the ball and the rod. The prosthesis further includes a brace which has both a cover plate and a base plate. The base plate has a seat which is specifically shaped to support the ball and the base plate is formed with an extension which can be affixed to the radius of the patient. With the base plate mounted on the radius, the cover plate of the brace is secured to the base plate with the ball held between the two plates to establish a relative rotational motion between the ball and the brace. With this overall structure, a relative general motion is established between the rod (ulna) and the brace (radius).

13 Claims, 2 Drawing Sheets

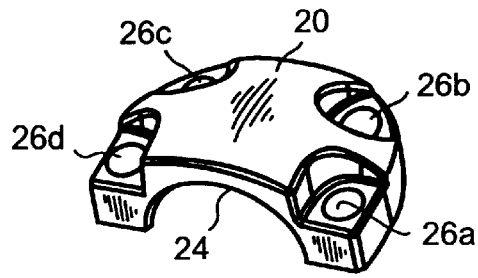
Figure 4
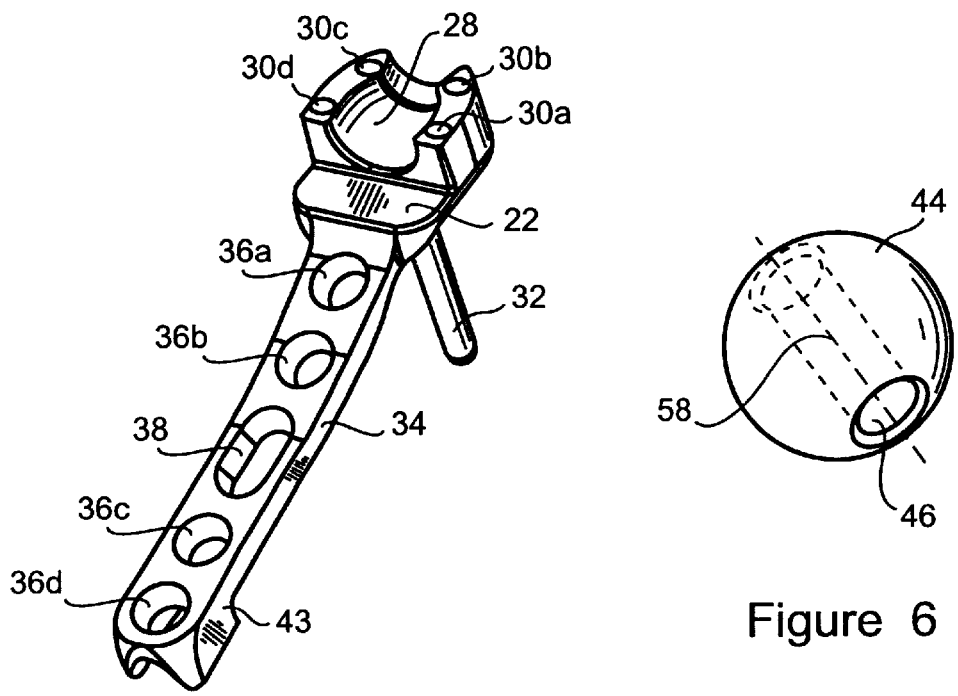
Figure 5
Figure 6
Figure 7

DISTAL RADIOULNAR JOINT PROSTHESIS

FIELD OF THE INVENTION

The present invention pertains generally to prostheses. More specifically, the present invention pertains to prostheses which require interactive components that are capable of relative motions which mimic anatomical movements. The present invention is particularly, but not exclusively, useful as a prosthesis device to the distal radioulnar joint of the wrist.

BACKGROUND OF THE INVENTION

Like other joints and anatomical features of the human body, the distal radioulnar joint is exceedingly complex in its make-up and function. Also like the other joints and anatomical features of the human body, the distal radioulnar joint is unique unto itself and requires specific considerations for its reconstruction or replacement. The complexity and uniqueness of this joint are quite interesting and are, perhaps, best appreciated by considering the skeletal motions which are involved in its movement.

A comparison of FIG. 1A and FIG. 1B in the drawings clearly shows that in the transition of the hand and forearm from pronation (FIG. 1A) to supination (FIG. 1B) the radius and ulna of the forearm transition from a crossed relationship to a side-by-side relationship. Thus, in this movement there is a relative rotation of the radius about the ulna. Also, but much more subtly, during the transition between pronation and supination there is some relative translational movement between the radius and ulna. The consequence of all this is that from a reference point on the ulna, the radius appears to move with a general motion that includes both translation and rotation. Obviously, if this anatomical movement of the distal radioulnar joint is to be duplicated, all of the dynamic components of the movement need to be accounted for and properly coordinated.

The importance of having a workable prosthesis device for the distal radioulnar joint is underscored by the debilitating effects which commonly result when the joint becomes diseased (e.g. arthritis) or destroyed by trauma. It is well known that after excision of the ulnar head, for whatever reason, both forearm bones collide and this is frequently associated with pain, instability or weakness, loss of motion, and loss of sensation on the ulnar side. It is, therefore, of great importance to the patient that these maladies be remedied.

In light of the above it is an object of the present invention to provide a prosthesis for the distal radioulnar joint of a patient which is capable of mimicking the general motion of the anatomical joint that is being replaced. Another object of the present invention is to provide a prosthesis for the distal radioulnar joint of a patient which is sturdy and robust in its operation and longevity. Yet another object of the present invention is to provide a prosthesis for the distal radioulnar joint which has increased range for pronation and supination. Still another object of the present invention is to provide a prosthesis for the distal radioulnar joint of a patient which is relatively easy to manufacture, is simple to use and is comparatively cost effective.

SUMMARY OF THE PREFERRED EMBODIMENTS

A prosthesis for the distal radioulnar joint of a patient includes a brace which is mounted on the radius of the patient, a rod which is attached to the patient's ulna, and a ball which is seated on the brace and engaged with the rod to provide for a general motion between the brace and the rod.

In detail, the brace includes a base plate and a cover plate. More specifically, the base plate is formed with a seat and an extension which is shaped to substantially conform with the radius. Additionally, the base plate has a peg which can be embedded into the radius. Thus, with the peg embedded into the radius, and the extension secured to the radius, the base plate is firmly held on the radius with the seat exposed.

The rod is elongated and has a fluted body portion which is engageable with the ulna. Specifically, the rod is engaged with the ulna by driving the body portion of the rod into the bone cavity of the ulna. The rod also has a pin at its end which is exposed when the rod is engaged with the ulna, and there is an abutment which is formed between the pin and the body portion.

Additionally, a ball is provided as part of the device for the present invention. Specifically, the ball is formed with a hollow channel that passes through the ball substantially along a diameter of the ball.

In the assembly of the prosthesis device for the present invention, the base plate of the brace is first secured to the radius, and the body portion of the rod is attached to the ulna. The ball is then connected with the rod by inserting the pin of the rod into the channel of the ball. This connection allows for relative translational movement between the ball and the rod. Next, the ball is positioned on the seat of the base plate and the cover plate is joined with the base plate to capture and hold the ball on the brace between the cover plate and the base plate.

In the operation of the prosthesis device for the distal radioulnar joint of the present invention, the rod is able to move in translation relative to the ball. Simultaneously, the ball is able to move in rotation with changing angle relative to the brace. Consequently, the rod moves in general motion relative to the brace to mimic the natural anatomical movement of the distal radioulnar joint.

BRIEF DESCRIPTION OF THE DRAWINGS

The novel features of this invention, as well as the invention itself, both as to its structure and its operation, will be best understood from the accompanying drawings, taken in conjunction with the accompanying description, in which similar reference characters refer to similar parts, and in which:

FIG. 4 is a perspective view of the cover plate of the brace for the present invention;

FIG. 5 is a perspective view of the base plate of the brace for the present invention;

FIG. 6 is a perspective view of the ball for the present invention with portions shown in phantom for clarity; and FIG. 7 is a side elevational view of the rod for the present invention.

DESCRIPTION OF THE PREFERRED EMBODIMENT

Figure 1A:
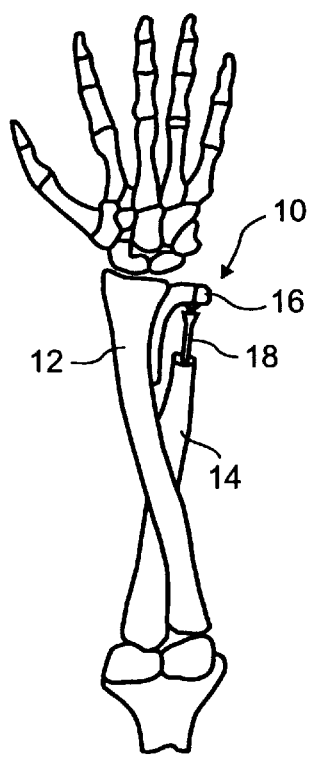
FIG. 1A is a skeletal representation of the human forearm in pronation.
Figure 1B:
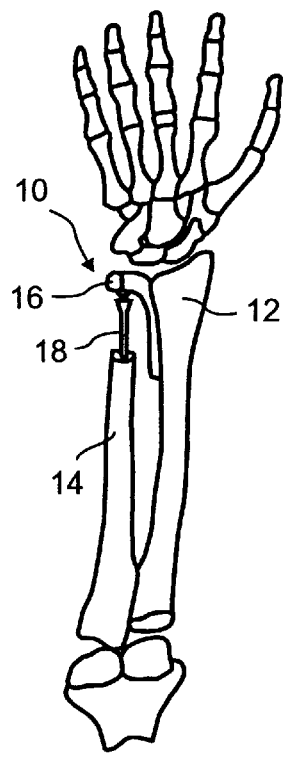
FIG. 1B is a skeletal representation of the human forearm in supination.

Referring initially to FIG. 1A and FIG. 1B, a prosthesis device for the distal radioulnar joint of a patient is shown and generally designated 10. As shown, the device 10 is intended to mimic the anatomical movement of the radius 12 and ulna 14 in patient's forearm as the patient moves between pronation (FIG. 1A) and supination (FIG. 1B). In overview, as shown in the FIGS. 1A and 1B, the device 10 includes a brace 16 which is mounted on the radius 12, and a rod 18 which is attached to the ulna 14.

Figure 2:
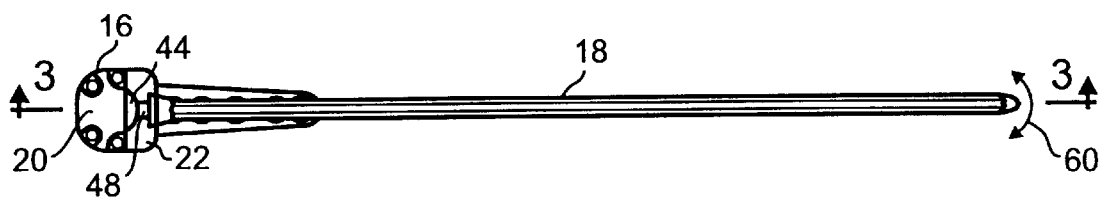
FIG. 2 is a top plan view of the prosthesis for the distal radioulnar joint of the present invention.
Figure 3:
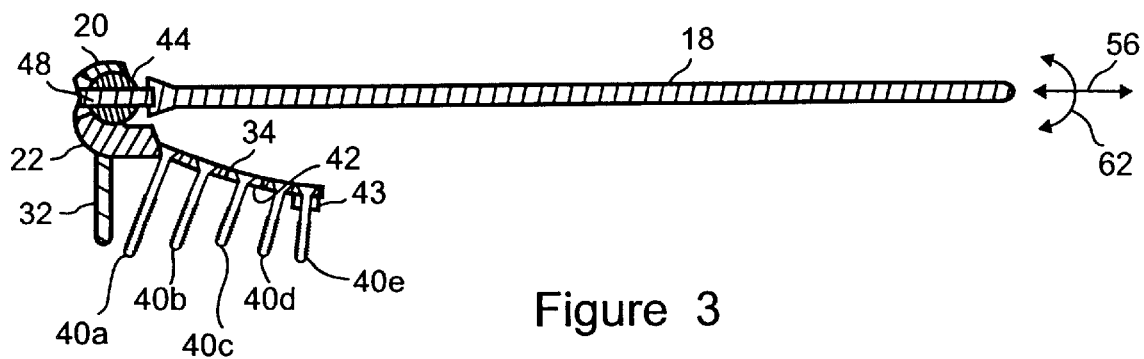
FIG. 3 is a cross sectional view of the prosthesis device of the present invention as seen along the line 3—3 in FIG. 2.

By cross referencing FIG. 2 with FIG. 3, it will be seen that the brace 16 includes a cover plate 20 and a base plate 22. As best seen in FIG. 4, the cover plate 20 is formed with a seat 24 which has a substantially spherical shaped surface. Additionally, the cover plate 20 is formed with a plurality of screw holes 26a–d. As best seen in FIG. 5, the base plate 22 is formed with a seat 28 which, like seat 24, has a spherical shaped surface. Additionally, base plate 22 is formed with a plurality of screw holes 30a–b substantially as shown. Importantly, the seat 28 is compatible in its dimensions with the seat 24 of cover plate 20 so that together they establish a substantially spherical shaped enclosure when the cover plate 20 is joined with the base plate 22.

FIG. 5 also shows that the base plate 22 includes a peg 32 which projects therefrom substantially as shown, and that the base plate 22 is formed with an extension 34 which includes holes 36a–d and a slot 38. If desired, the peg 32 can be modified and used with, or replaced by, a tap for receiving a screw (not shown). As intended for the present invention, the holes 36 and slot 38 are provided for respectively receiving the screws 40a–e therethrough. Also, it is to be appreciated that the surface 42 of extension 34 is curved, and that extension 34 is formed with a saddle 43, so that it will substantially conform with, and stabilize on, the radius 12 when the base plate 22 is mounted on the radius 12. It is to be appreciated, however, that saddle 43 could be eliminated or varied so that the surface 42 is uniformly flat or has some intermediate shaped configuration.

Referring back to FIGS. 2 and 3, it will be seen that the device 10 also includes a ball 44 which is used to interconnect the brace 16 with the rod 18. In FIG. 6 it will be seen that this ball 44 is formed with a hollow channel 46 which extends through the ball 44 substantially along a diameter of ball 44. Preferably, the ball 44 is made of a material that is commercially available and known in the pertinent art as ultra high molecular weight polyethylene (UHMWPE).

In FIG. 7 it will be seen that the rod 18 is formed with a pin at one end and that there is an elongated body portion 50 which generally defines a longitudinal axis. Further, the rod 18 is formed with an abutment 52 that is located between the pin 48 and the body portion 50. It is to also be appreciated that the body portion 50 is formed with a plurality of flutes 54 that are formed into the body portion 50 and extend substantially along the entire length of the body portion 50.

For the assembly of the device 10, and its implantation into the patient, the patient is properly prepared and the base plate 22 is then positioned on the radius 12 as desired. Typically, this positioning will be as substantially shown in FIGS. 1A and 1B. When so positioned, the peg 32 will be embedded into the radius 12 and the extension 34 will be affixed to the radius 12 by the screws 40a–d. Next, the rod 18 is attached to the ulna 14 by inserting the body portion 50 of the rod 18 into the bone cavity of the ulna 14. This will leave the pin 48 of the rod 18 open and exposed. It is to be appreciated that, in accordance with the present invention, the attachment of the rod 18 can be done first, before base plate 22 is positioned on the radius 12, to reverse the order of these operations.

Once the base plate 22 is in place on the radius 12, and the rod 18 is attached to the ulna 14, the ball 44 is positioned on the rod 18. Specifically, this is done by inserting the pin 48 of rod 18 into the channel 46 of ball 44. As intended for the present invention, the pin 48 is slidingly positioned in the channel 46 so that the pin 48 is able to reciprocally move in translation relative to the ball 44 back and forth in the directions indicated in FIG. 3 by the arrow 56. Incidentally, due to the sliding interface between the pin 48 and the ball 44, the ball 44 is able to rotate on the pin 48 around the longitudinal axis of the body portion 50 of rod 18.

With the ball 44 positioned on pin 48 of rod 18, the ball 44 is then positioned on the seat 28 of base plate 22. When the ball 44 is so positioned, the cover plate 20 is secured to the base plate 22 to hold the ball 44 between the seat 24 of cover plate 20 and the seat 28 of base plate 22. Specifically, the cover plate 20 is secured to the base plate 22 by a plurality of fasteners, such as screws (not shown) which are respectively inserted through the screw holes 26a–d in cover plate 20, and into the screw holes 30a–d of base plate 22. Thus, the brace 16 is created which holds the center 58 of the ball 44 in a fixed relationship with the radius 12 while allowing the ball 44 to rotate about the center 58. With the ball 44 captured by brace 16, the rod 18 (and ball 44) are allowed to rotate relative to the brace 16 in the directions indicated by arrow 60 in FIG. 2 and arrow 62 in FIG. 3.

According to the structure disclosed above for the device 10 it is to be appreciated that with the combination of translational movement of the rod 18 relative to the ball 44, and rotational movement of the ball 44 relative to the brace 16, there is a general motion of the rod 18 relative to the brace 16. It happens that this general motion mimics the anatomical movement of the distal radioulnar joint which the device 10 is intended to replace.

While the particular distal radioulnar joint prosthesis as herein shown and disclosed in detail is fully capable of obtaining the objects and providing the advantages herein before stated, it is to be understood that it is merely illustrative of the presently preferred embodiments of the invention and that no limitations are intended to the details of construction or design herein shown other than as described in the appended claims.

What is claimed is:

1. A prosthesis for a distal radioulnar joint which comprises:

an elongated rod formed with a pin;

a ball formed with a channel for slidingly receiving said pin therein for relative translational motion between said ball and said rod;

a base plate; and a cover plate engageable with said base plate for holding said ball on said base plate for relative rotational motion between said ball and said base plate.

2. A prosthesis device as recited in claim 1 wherein said rod has an elongated body portion and said pin is substantially coaxial with said body portion, and wherein said rod further comprises an abutment formed between said pin and said body portion for limiting relative translational motion therebetween.

3. A prosthesis device as recited in claim 2 wherein said body portion is formed with a plurality of flutes longitudinally oriented thereon.

4. A prosthesis device as recited in claim 1 wherein said ball is made of ultra high molecular weight polyethylene (UHMWPE).

5. A prosthesis device as recited in claim 1 further comprising a peg extending from said base plate.

6. A prosthesis device as recited in claim 1 wherein said base plate is mounted on the radius bone of a patient.

7. A prosthesis device as recited in claim 6 wherein said rod is attached to the ulna bone of the patient.

8. A prosthesis device for a distal radioulnar joint which comprises:
- a rod having a first end formed as a pin and a second end, said second end of said rod being attached to the ulna bone of a patient;
- a ball formed with a channel for slidingly receiving said pin therein for relative translational motion between said ball and said rod; and
- a brace having a first end and a second end, said second end of said brace being mounted on the radius bone of the patient, and said first end of said brace being engaged with said first end of said rod for relative general motion therebetween.

9. A device as recited in claim 8 wherein said brace comprises:
- a base plate; and
- a cover plate engeagable with said base plate for holding said ball on said base plate for relative rotational motion between said ball and said base plate.

10. A device as recited in claim 9 wherein said rod has an elongated body portion and said pin is substantially coaxial with said body portion, and wherein said rod further comprises an abutment formed between said pin and said body portion for limiting relative translational motion therebetween.

11. A prosthesis device as recited in claim 10 wherein said body portion is formed with a plurality of flutes longitudinally oriented thereon and wherein said ball is made of ultra high molecular weight polyethylene (UHMWPE).

12. A prosthesis device as recited in claim 11 further comprising a peg extending from said base plate.

13. A method for establishing a prosthesis in a patient for a distal radioulnar joint which comprises the steps of:
- attaching a rod to the ulna of a patient, the rod having a first end formed as a pin and a second end formed as a body portion substantially coaxial with said pin, with the attachment being made by inserting said body portion into the ulna;
- providing a ball formed with a channel;
- inserting said pin of said rod into said channel of said ball for relative translational motion between said ball and said rod;
- mounting a base plate on the radius bone of the patient; and
- securing a cover plate to said base plate for holding said ball on said plate for relative rotational motion between said ball and said base plate.

* * * * *